(12) United States Patent
Martin

(10) Patent No.: US 11,717,162 B2
(45) Date of Patent: Aug. 8, 2023

(54) REBOUND TONOMETER HAVING TILT CORRECTION

(71) Applicant: Reichert, Inc., Depew, NY (US)

(72) Inventor: Gabriel Norberto Martin, Buenos Aires (AR)

(73) Assignee: Reichert, Inc., Depew, NY (US)

( * ) Notice: Subject to any disclaimer, the term of this patent is extended or adjusted under 35 U.S.C. 154(b) by 631 days.

(21) Appl. No.: 16/645,523

(22) PCT Filed: Sep. 11, 2018

(86) PCT No.: PCT/US2018/050346
§ 371 (c)(1),
(2) Date: Mar. 9, 2020

(87) PCT Pub. No.: WO2019/055374
PCT Pub. Date: Mar. 21, 2019

(65) Prior Publication Data
US 2020/0196864 A1    Jun. 25, 2020

Related U.S. Application Data

(60) Provisional application No. 62/557,553, filed on Sep. 12, 2017.

(51) Int. Cl.
*A61B 3/16* (2006.01)
*A61B 3/00* (2006.01)

(52) U.S. Cl.
CPC .............. *A61B 3/16* (2013.01); *A61B 3/0025* (2013.01); *A61B 2560/0238* (2013.01)

(58) Field of Classification Search
CPC ....... A61B 3/16; A61B 3/1241; A61B 3/0025; A61B 2560/0219; A61B 5/031;
(Continued)

(56) References Cited

U.S. PATENT DOCUMENTS

2002/0010393 A1    1/2002  Israel
2004/0260168 A1    12/2004 Shimmyo
(Continued)

FOREIGN PATENT DOCUMENTS

CN       104274153 A      1/2015
DE    102004001675 A1     8/2005
(Continued)

*Primary Examiner* — Brandi N Thomas
(74) *Attorney, Agent, or Firm* — Hodgson Russ LLP

(57) ABSTRACT

A rebound tonometer is improved by providing a tilt signal from a tilt sensor of the rebound tonometer to a signal processor of the rebound tonometer, and configuring the signal processor to apply a tilt correction factor to a basic IOP measurement value calculated by the signal processor to provide a final IOP measurement value, wherein the tilt correction factor depends on a tilt direction and a degree of tilt indicated by the tilt signal. The final reported IOP measurement value takes into account gravitational effects on the probe due to tilt. As a result, measurements made at relatively small tilt angles are now usable, thereby improving efficiency. A corresponding rebound tonometry measurement method, and a method of calibrating a rebound tonometer for tilt correction, are also disclosed.

7 Claims, 3 Drawing Sheets

(58) Field of Classification Search
CPC ........... A61B 3/14; A61B 5/6814; A61B 3/10; A61B 5/4839; A61B 8/06; A61B 2562/0238; A61B 5/0002; A61B 5/14532; A61B 2560/0214; A61B 2560/0252; A61B 2560/0418; A61B 3/165; A61B 5/01; A61B 5/14539; A61B 5/14546; A61B 5/1455; A61B 5/14555; A61B 5/1486; A61B 5/18; A61B 5/416; A61B 5/445; A61B 8/56; A61B 3/0058; A61B 2562/12; A61B 3/185; A61B 5/14507; A61B 5/412; A61B 3/0083; A61B 2562/0261; A61B 5/1116; A61B 5/6803; A61B 5/6898; A61B 3/0008; A61B 5/411; A61B 5/0205; A61B 5/076; A61B 5/7275; A61B 2562/0266; A61B 2562/164; A61B 3/145; A61B 5/0013; A61B 5/4842; A61B 5/4884; A61B 5/686; A61B 3/107; A61B 5/021; A61B 2560/0261; A61B 5/0059; A61B 5/02416; A61B 5/1071; A61B 5/11; A61B 5/7278; A61B 8/10; A61B 2560/0238; A61B 3/102; A61B 3/12; A61B 3/0016; A61B 3/103; A61B 5/026; A61B 2503/40; A61B 2503/42; A61B 3/028; A61B 5/0031; A61B 5/0077; A61B 5/024; A61B 5/02438; A61B 5/055; A61B 5/1032; A61B 5/1077; A61B 5/1118; A61B 5/14542; A61B 6/50; A61B 2560/0276; A61B 2562/0247; A61B 2562/028; A61B 3/00; A61B 3/0091; A61B 3/152; A61B 18/18; A61B 18/22; A61B 3/117; A61B 3/125; A61B 3/18; A61B 5/0004; A61B 5/03; A61B 5/6861; A61B 90/30; A61B 2017/00725; A61B 2090/064; A61B 2090/3735; A61B 2090/502; A61B 2560/0223; A61B 2560/0247; A61B 2560/0257; A61B 2560/0456; A61B 2560/063; A61B 2562/0223; A61B 2562/168; A61B 3/0075; A61B 3/1225; A61B 34/10; A61B 5/00; A61B 5/0015; A61B 5/002; A61B 5/0066; A61B 5/0068; A61B 5/0075; A61B 5/02216; A61B 5/0261; A61B 5/0285; A61B 5/036; A61B 5/1075; A61B 5/1126; A61B 5/16; A61B 5/163; A61B 5/165; A61B 5/24; A61B 5/4082; A61B 5/4088; A61B 5/6867; A61B 5/7246; A61B 5/7264; A61B 8/0891; A61B 8/488; A61B 8/5207; A61B 8/5223; A61B 8/5261; A61B 8/58; A61B 90/06; A61F 9/0017; A61F 9/00781; A61F 9/0026; A61F 2/14; A61F 9/00825; A61F 2009/00891; A61F 9/00; A61F 2009/00868; A61F 2009/00872; A61F 9/0079; A61F 9/0008; A61F 2009/0052; A61F 2009/00851; A61F 9/00802; A61F 9/029; A61F 2/1451; A61F 9/00736; A61F 9/008; A61F 9/0081; A61F 9/00831; A61F 9/00834; A61F 9/009; A61F 2009/00848; A61F 2009/00865; A61F 2009/0087; A61F 2210/0076; A61F 2250/0002; A61F 9/007; A61F 9/00821; A61F 9/00827; A61F 9/00836; A61F 2/142; A61F 2/16; A61F 2/1613; A61F 2/1616; A61F 2002/1683; A61F 2009/00855; A61F 2009/00878; A61F 2009/00882; A61F 2009/00887; A61F 2009/00897; A61F 2250/0001; A61F 2250/0018; A61F 9/0084; A61F 9/013; A61P 27/06; A61P 27/02; A61P 43/00; A61P 29/00; A61P 35/00; A61P 9/00; A61P 9/10; A61P 31/00; A61P 3/10; A61P 27/00; A61P 31/04; A61P 27/12; A61P 25/28; A61P 25/00; A61P 21/00; A61P 25/16; A61P 27/10; A61P 9/02; A61P 11/00; A61P 11/08; A61P 25/02; A61P 27/04; A61P 37/06; A61P 9/12; A61P 11/02; A61P 11/06; A61P 11/14; A61P 25/08; A61P 27/14; A61P 3/04; A61P 31/14; A61P 31/20; A61P 37/02; A61P 39/06; A61P 7/02; A61P 13/12; A61P 17/00; A61P 17/02; A61P 19/02; A61P 21/02; A61P 27/16; A61P 29/02

See application file for complete search history.

(56) References Cited

U.S. PATENT DOCUMENTS

| | | | |
|---|---|---|---|
| 2007/0016254 A1 | 1/2007 | Grenon et al. | |
| 2008/0103381 A1 | 5/2008 | Kontiola | |
| 2012/0108941 A1* | 5/2012 | Maggiano | A61B 3/10 600/405 |
| 2014/0222363 A1 | 8/2014 | Ferran et al. | |
| 2016/0174838 A1* | 6/2016 | Herranen | A61B 3/16 351/246 |

FOREIGN PATENT DOCUMENTS

| | | |
|---|---|---|
| WO | 2017/035406 A2 | 3/2017 |
| WO | 2017/103330 A1 | 6/2017 |

* cited by examiner

A - Aligned

B - Aligned

REBOUND TONOMETER HAVING TILT CORRECTION

FIELD OF THE INVENTION

The present invention relates to rebound tonometers for measuring intraocular pressure (IOP).

BACKGROUND OF THE INVENTION

A rebound tonometer is a hand-held instrument that propels a movable measurement probe in a controlled manner toward the cornea of an eye to measure intraocular pressure and/or corneal biomechanics. The measurement probe is a disposable item typically having an elongated shaft terminating in a rounded tip. A new sterile measurement probe is loaded in the rebound tonometer prior to taking measurements on a patient. During a measurement, the probe contacts the cornea, is decelerated at a rate which depends on intraocular pressure, and then rebounds in a direction away from the cornea back toward the instrument housing. The rebound tonometer detects the motion of the measurement probe and determines intraocular pressure based on the detected motion of the probe. For example, the measurement probe may have a magnetized shaft which travels within a coil in the instrument housing. The coil may be energized momentarily to propel the probe toward the cornea by electromagnetic force, and then, after energizing current to the coil is shut off, a current may be induced in the coil by the moving probe to provide a detectable voltage signal (a measurement signal) representing motion of the probe. After measurements have been taken on a patient, the used measurement probe is discarded.

The measurement accuracy of a rebound tonometer is dependent upon alignment of the instrument with the eye. Theoretically, for greatest accuracy, a travel axis of the probe (the measurement axis) should coincide with a central optical axis of the eye and the probe should travel a predetermined working distance along the measurement axis before contacting the eye at or very close to the corneal apex. To help with alignment and stability, it is known to provide an adjustable forehead support above the probe mechanism. The forehead support protrudes from the tonometer housing, and a distal end of the forehead support may be placed against the patient's forehead to establish a proper working distance. It is also known to equip a rebound tonometer with a sensing system capable of evaluating alignment and providing a yes or no indication of alignment to the user. Nevertheless, considerable skill and time is required to properly align the measurement axis to the eye. Because several (e.g. six) measurements may be recommended per eye and extra readings are often needed to refine alignment, rebound tonometry is sometimes considered inefficient.

The position of the patient's head and direction of the patient's gaze may complicate alignment. If the patient's head is tilted and/or the patient's gaze is fixated along a direction that is inclined relative to horizontal, then the measurement axis cannot be properly aligned with the eye without tilting the rebound tonometer so the measurement axis is also inclined. However, if the measurement axis along which the probe travels is tilted to have a vertical component, the effects of gravity on the probe's motion may decrease measurement accuracy. U.S. Patent Application Publication No. 2016/0174838 teaches a rebound tonometer in which a tilt sensor (i.e. an inclinometer) is used to alert the operator prior to measurement that the measurement axis is inclined so that the operator may eliminate the inclination by repositioning the rebound tonometer and/or the patient so that the measurement axis is horizontal. However, if a measurement is made while the measurement axis is tilted, the accuracy of the measurement suffers due to the mentioned gravitational effects.

SUMMARY OF THE INVENTION

A rebound tonometer is improved by providing a tilt signal from a tilt sensor of the rebound tonometer to a signal processor of the rebound tonometer, and configuring the signal processor to apply a tilt correction factor to a basic IOP measurement value calculated by the signal processor to provide a final IOP measurement value, wherein the tilt correction factor depends on a tilt direction and a degree of tilt indicated by the tilt signal. In this way, the final reported IOP measurement value takes into account gravitational effects on the probe due to tilt. As a result, measurements made at relatively small tilt angles are now usable, thereby improving efficiency and usability.

A rebound tonometry method according to the present disclosure generally comprises the steps of operating a rebound tonometer to propel a measurement probe along a measurement axis toward an eye of a test subject such that the measurement probe is rebounded by the eye in a direction away from the eye, detecting measurement data describing motion of the measurement probe toward and away from the eye, sensing a direction and a degree of tilt of the measurement axis when the measurement probe is propelled toward the eye, calculating a basic IOP measurement value from the measurement data, and applying a tilt correction factor to the basic IOP measurement value to yield a final IOP measurement value, wherein the tilt correction factor depends on the direction and the degree of tilt.

The present disclosure also provides a method of calibrating a rebound tonometer generally comprising the steps of operating the rebound tonometer at predetermined tilt angles of the measurement axis to measure pressure of a simulated eye having a known pressure to determine a difference between the measured pressure and the known pressure, and storing information for determining an applicable tilt correction factor corresponding to each of the predetermined tilt angles, wherein application of the applicable tilt correction factor to the measured pressure at the corresponding predetermined tilt angle yields the known pressure, and wherein the stored information is available during normal use of the calibrated rebound tonometer.

BRIEF DESCRIPTION OF THE DRAWING VIEWS

The nature and mode of operation of the present invention will now be more fully described in the following detailed description of the invention taken with the accompanying drawing figures, in which.

DETAILED DESCRIPTION OF THE INVENTION

The present disclosure relates to improving a rebound tonometer by incorporating a tilt sensor to compensate for gravity effects when a measurement axis of a rebound tonometer is tilted from horizontal during a measurement.

Figure 1:
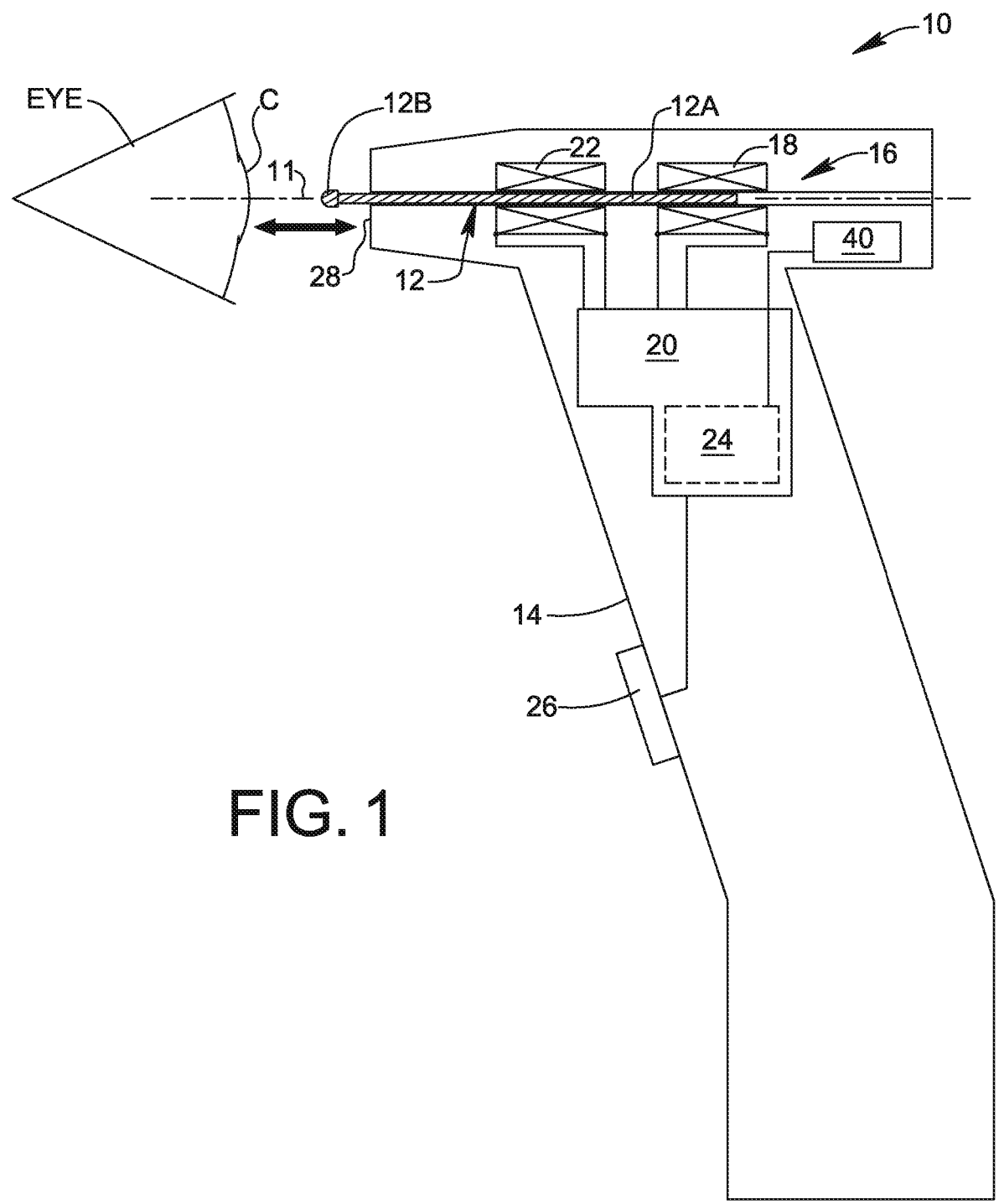
FIG. 1 is a schematic view of a rebound tonometer having tilt correction in accordance with an embodiment of the present invention

FIG. 1 is a schematic view showing a rebound tonometer 10 formed in accordance with an embodiment of the present invention. Rebound tonometer 10 generally comprises a disposable probe 12 and a hand-held housing 14 containing a measurement system 16 configured to propel probe 12 in a forward direction along a measurement axis 11 toward an eye of test subject, wherein probe 12 contacts a cornea C of the eye and is rebounded from the cornea in a reverse direction opposite the forward direction.

Probe 12 may include an elongated shaft 12A, at least a portion of which is made of a magnetic material, and a rounded tip 12B at an end of shaft 12A for contacting cornea C. Measurement system 16 may include a conductive drive coil 18 in which probe 12 is received, and a controller 20 configured to momentarily energize drive coil 18 to propel probe 12 forward toward the eye by electromagnetic force. Measurement system 16 may include a conductive measurement coil 22 through which probe 12 moves, and controller 20 may be further configured to measure a current induced in measurement coil 22 by the moving probe 12 and provide a measurement signal representing velocity of the probe as a function of time. For example, controller 20 may be configured to receive the current induced in measurement coil 22 by the moving probe 12 and provide an analog voltage signal as the measurement signal. The embodiment depicted in FIG. 1 shows drive coil 18 and measurement coil 22 as being two different conductive coils. Alternatively, a single coil may act sequentially during a measurement cycle as both the drive coil and the measurement coil, thus eliminating the need for a second coil.

As known in the art of rebound tonometers, instrument 10 may further comprise an opto-electronic alignment detection system (not shown) and a display (not shown) to guide and confirm alignment of a measurement axis 11 of instrument 10 with cornea C and positioning of a front nose 28 of instrument 10 at a predetermined working distance from cornea C. A trigger button 26 may be provided on housing 14 for enabling a user to send a signal to controller 20 to initiate a measurement, and/or the alignment detection system may automatically send a signal to controller 20 to initiate a measurement when alignment and proper working distance are confirmed by the alignment detection system.

Measurement system 16 further includes a signal processor 24, which may be part of controller 20 as shown in FIG. 1. Signal processor 24 may be configured to convert the analog measurement signal to digital form, and to calculate a basic IOP measurement value from the digitized measurement signal. For example, signal processor logic 20 may comprise an analog-to-digital signal converter and a programmed microprocessor for executing instructions stored in memory for calculating the basic IOP measurement value.

Figure 2:
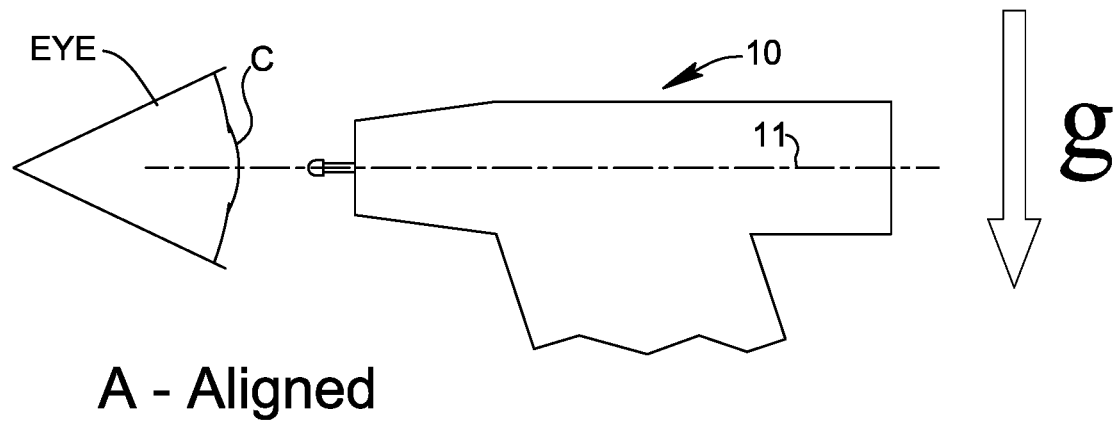
FIG. 2 is a side view illustrating proper alignment of a rebound tonometer with an eye of a test subject, wherein a measurement axis of the rebound tonometer is horizontal.
Figure 3:
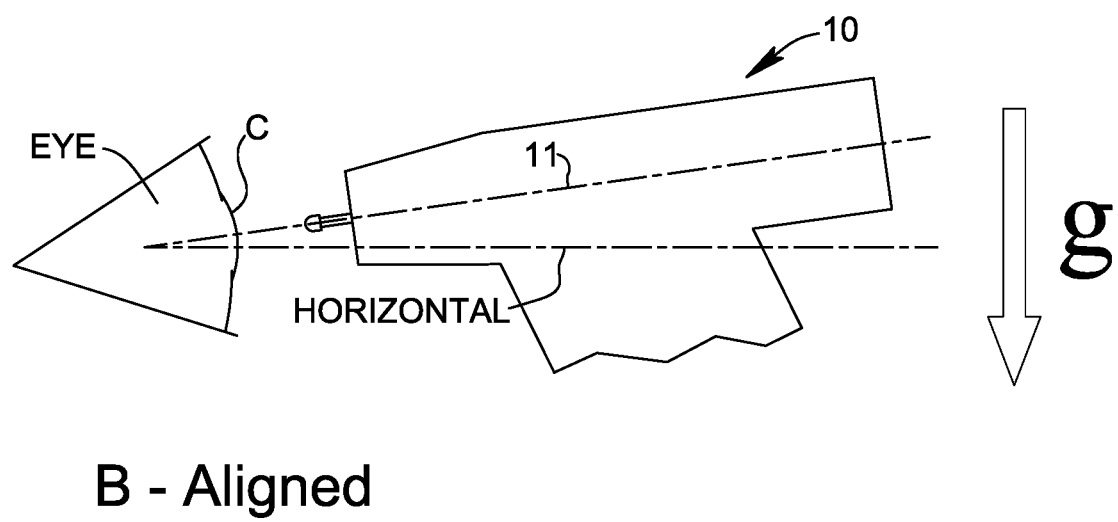
FIG. 3 is another side view also illustrating proper alignment of a rebound tonometer with an eye of a test subject, but the measurement axis is tilted from horizontal.

Reference is now made to FIGS. 2 and 3. FIG. 2 is a side view illustrating proper alignment of rebound tonometer 10 with an eye of a test subject, wherein measurement axis 11 of rebound tonometer 10 is horizontal. As may be seen, gravity force "g" acts perpendicular to the direction of motion of the tonometer's rebound probe 12 along measurement axis 11. Consequently, gravity force "g" does not have any component acting in the direction of motion of probe 12 that may influence the velocity at which the probe impacts the cornea and thereby affect the measurement result.

FIG. 3 is another side view which also illustrates proper alignment of a rebound tonometer 10 with an eye of a test subject. However, in FIG. 3, the test subject's gaze direction is tilted slightly upward such that proper alignment requires that measurement axis 11 also be tilted from horizontal. In this situation, gravity force "g" includes a component acting in the direction of motion of the probe. As may be understood from FIG. 3, the gravity component will accelerate the probe as it travels toward the eye, causing the probe to impact the eye at a velocity greater than a desired predetermined velocity. Of course, if the test subject's gaze direction is tilted downward rather than upward, the probe will be decelerated by gravity as it travels toward the eye.

In order to compensate for effects of gravity where measurement axis 11 is tilted from horizontal, rebound tonometer 10 may be equipped with a tilt sensor 40 as shown in FIG. 1. Tilt sensor 40 may be integrated in controller 20 or may be separate from controller 20 as depicted in FIG. 1. Tilt sensor 40 generates a tilt signal indicating a direction (i.e. upward or downward) and degree of tilt of measurement axis 11 at the time a measurement is initiated. Tilt sensor 40 may be connected to signal processor 24 for processing the measurement signal representing motion of probe 12 to determine IOP. The tilt signal from tilt sensor 40 may be provided to signal processor 24 and taken into account in the calculation of IOP to compensate for the unwanted effects of gravity on the measurement. By way of non-limiting example, tilt sensor 40 may be embodied as a Bosch Sensortec BMA253 triaxial, low-g acceleration sensor with digital output.

Figure 4:
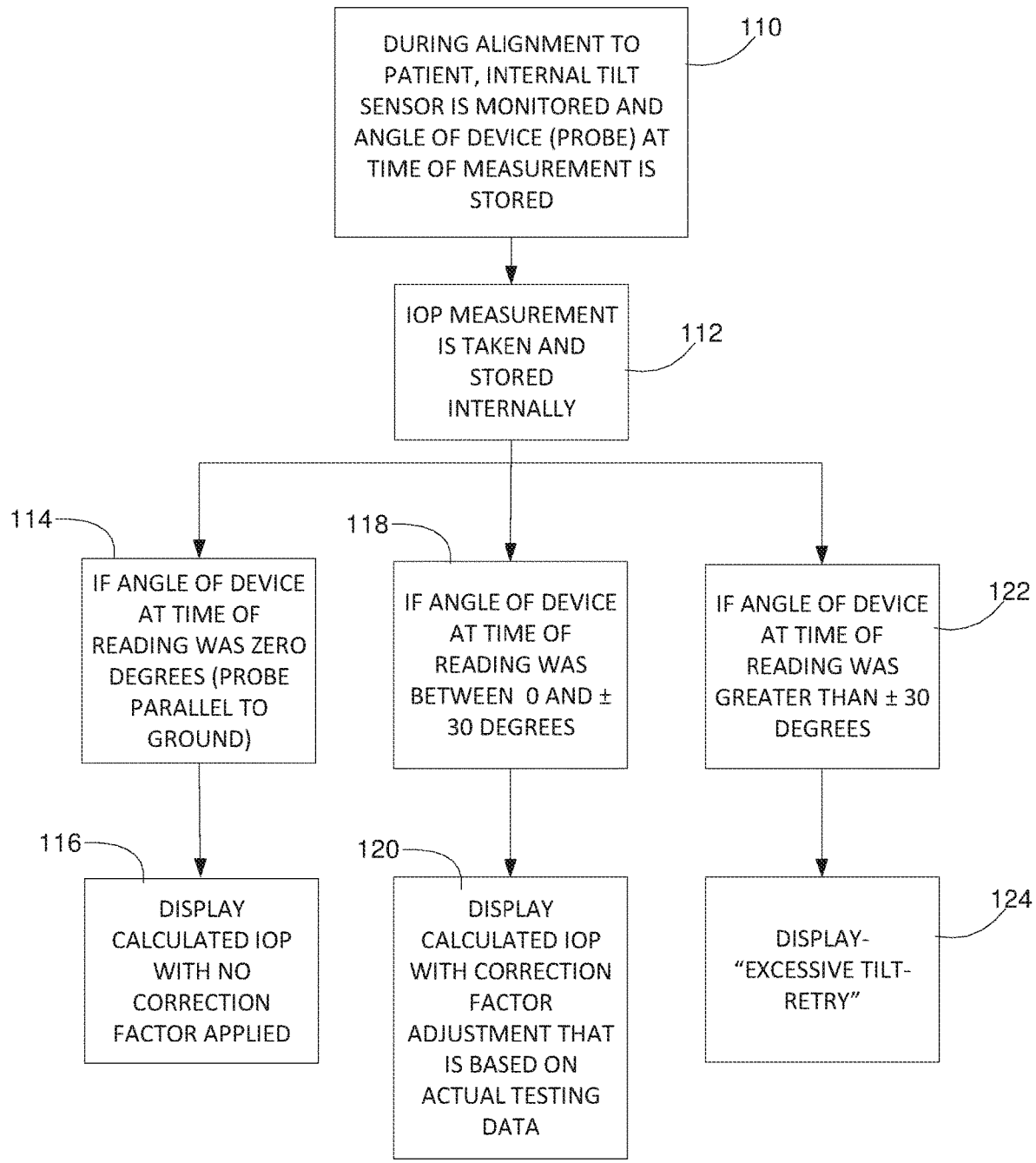
FIG. 4 is a flow diagram illustrating logic used by the rebound tonometer of FIG. 11 to compensate for effects of gravity due to tilting.

FIG. 4 is a flow diagram illustrating an example of logic followed by signal processor 24 of rebound tonometer 10 to compensate for effects of gravity due to tilting. The logic may be embodied by software code stored in memory in rebound tonometer 10 and executed by signal processor 24. As shown in block 110, tilt sensor 40 is monitored during an IOP measurement and the tilt angle of measurement axis 11 and probe 12 at the time of measurement is stored in memory. The IOP measurement is also taken and stored in memory pursuant to block 112. Flow may then branch to one of three flow paths depending upon the sensed tilt angle. If the tilt angle is zero or nearly zero in accordance with block 114, then the measured IOP is calculated without applying a tilt correction factor and is displayed as indicated by block 116. If the tilt angle is between zero degrees and relatively low tilt angle, for example ±30 degrees in accordance with block 118, then the IOP is calculated and adjusted by applying a tilt correction factor based on the sensed tilt angle to provide a final IOP measurement result, which is displayed as indicated by block 120. The tilt correction factor may be empirically determined in a calibration step by operating tonometer 10 at predetermined tilt angles using a simulated eye of known pressure, and a look-up table of applicable correction factors for various tilt angles may be stored in memory for use in block 120. Instead of a look-up table, a tilt correction function may be stored in memory for enabling calculation of an appropriate tilt correction factor based on the tilt signal. Application of the tilt correction factor may simply be addition of the tilt correction factor, which may be positive or negative, to the basic IOP measurement value. If the tilt angle is outside the acceptable range, for example its absolute value is greater than 30 degrees in accordance with block 122, then an error message is displayed such as "Excessive Tilt—Retry" as indicated in block 124.

As will be appreciated from the foregoing description, rebound tonometer 10 disclosed herein corrects for tilting of the measurement axis 11 during a measurement. This improvement allows more test subjects to be measured in a given period of time with greater measurement accuracy because slight inclination of the test subject's gaze does not disqualify measurements as in the prior art.

What is claimed is:

1. In a rebound tonometer having a hand-held body, a measurement axis, a probe, means for propelling the probe along the measurement axis toward an eye of a test subject such that the probe contacts and rebounds from the eye, means for generating a measurement signal representing motion of the probe, a signal processor configured to calculate a basic TOP measurement value based on the measurement signal, and a tilt sensor for detecting tilt of the measurement axis relative to horizontal, the improvement comprising:

the tilt sensor being configured to generate a tilt signal indicating a direction and a degree of tilt of the measurement axis relative to horizontal when the probe is propelled toward the eye, wherein the tilt sensor is connected to the signal processor and the tilt signal is provided to the signal processor; and the signal processor being configured to apply a tilt correction factor to the basic TOP measurement value to provide a final TOP measurement value, wherein the tilt correction factor depends on the direction and the degree of tilt indicated by the tilt signal.

2. The improvement according to claim 1, wherein rebound tonometer has a memory connected to the signal processor, and the tilt correction factor is stored in the memory.

3. The improvement according to claim 2, wherein the tilt correction factor is empirically determined during calibration of the rebound tonometer.

4. The improvement according to claim 1, wherein the signal processor is configured to apply the tilt correction factor only if the degree of tilt indicated by the tilt signal is within a predetermined angular range.

5. The improvement according to claim 1, wherein the means for propelling the probe includes a conductive coil energizable to propel the probe along the measurement axis toward an eye of a test subject.

6. The improvement according to claim 1, wherein the means for generating the measurement signal includes a conductive coil through which the probe moves and induces current.

7. The improvement according to claim 1, wherein the means for propelling the probe and the means for generating the measurement signal together include only a single conductive coil, wherein the single conductive coil is energizable to propel the probe, and movement of the probe through the single conductive coil induces current to generate the measurement signal.

* * * * *